United States Patent [19]
Arita et al.

[11] Patent Number: 4,600,766
[45] Date of Patent: Jul. 15, 1986

[54] PROCESS FOR PRODUCING CROSS-LINKED RESIN FROM BIS(2-OXAZOLINE) AND AROMATIC HYDROXY-CARBOXYLIC ACID

[75] Inventors: Kazuhiro Arita, Takatsuki; Isao Masuda, Shimizu; Yasuo Sano, Minoo, all of Japan

[73] Assignee: Takeda Chemical Industries, Ltd., Osaka, Japan

[21] Appl. No.: 660,488

[22] Filed: Oct. 11, 1984

[30] Foreign Application Priority Data

Oct. 21, 1983 [JP] Japan ................................ 58-198121

[51] Int. Cl.$^4$ ............................................. C08G 73/00
[52] U.S. Cl. .................................... 528/207; 528/172; 528/208; 528/271; 528/313; 528/322; 528/373; 528/377; 528/378; 528/391; 528/423
[58] Field of Search ........................ 528/208, 207, 363

[56] References Cited
U.S. PATENT DOCUMENTS 3,476,712 11/1969 Fukui et al. ........................... 528/363
4,474,942 10/1984 Sano et al. ........................... 528/363

Primary Examiner—Harold D. Anderson
Attorney, Agent, or Firm—Wenderoth, Lind & Ponack

[57] ABSTRACT

A process for producing a novel cross-linked resin which comprises: reacting a bis(2-oxazoline) compound with a reactive compound which has at least one active hydrogen in the molecule, the reactive compound being at least one selected from the group consisting of a sulfonamide, an acid imide, an aromatic hydroxy-carboxylic acid and a bisphenol sulfone compound, in a molar ratio of the reactive compound to the bis(2-oxazoline) compound of not more than about 2, at an elevated temperature. About 5 to about 95 mole % of the reactive compound is replaceable by a dicarboxylic acid.

The cross-linked resin may be usable for the production of machinery parts such as rolls and gears and embedded moldings of electrical machinery and apparatus parts as well as for electric insulating materials and dental uses. The cross-linked resin may further find applications in, for example, adhesives and various coating compositions.

23 Claims, No Drawings

PROCESS FOR PRODUCING CROSS-LINKED RESIN FROM BIS(2-OXAZOLINE) AND AROMATIC HYDROXY-CARBOXYLIC ACID

This invention relates to a process for producing novel cross-linked resins.

It is already known, as disclosed in U.S. Pat. No. 3,476,712, that the reaction of a bis(2-oxazoline) compound with a dicarboxylic acid in an equimolar amount under heating produces linear polyesteramides.

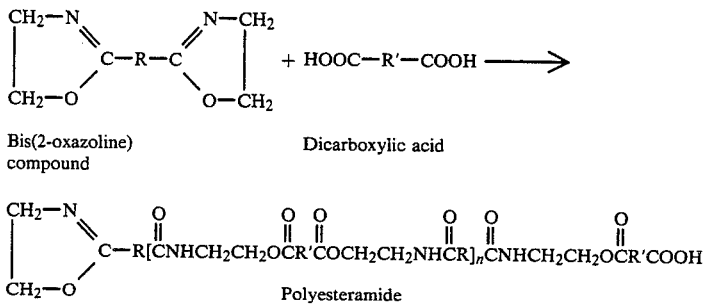

However, no thermosetting resin has hitherto been known which is formed by the reaction of a bis(2-oxazoline) compound and a reactive compound which has at least one active hydrogen in the molecule such as a sulfonamide, an acid imide, an aromatic hydroxy-carboxylic acid or a bisphenol sulfone compound.

The present inventors have made an intensive investigation on the reaction of a bis(2-oxazoline) compound with the reactive compound as above, and have found that the reaction in a molar ratio of the reactive compound to the bis(2-oxazoline) of not more than about 2 at an elevated temperature readily provides a novel three-dimensionally cross-linked resin which has especially a high heat-resistance and a very small water-absorptivity.

It is therefore an object of the invention to provide a process for producing novel cross-linked resins.

The process for producing cross-linked resins of the invention comprises: reacting a bis(2-oxazoline) compound with a reactive compound which has at least one active hydrogen in the molecule, the reactive compound being at least one selected from the group consisting of a sulfonamide, an acid imide, an aromatic hydroxy-carboxylic acid and a bisphenol sulfone compound, in a molar ratio of the reactive compound to the bis(2-oxazoline) compound of not more than about 2, at an elevated temperature.

The bis(2-oxazoline) compound used in the present invention has the general formula:

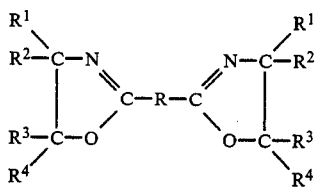

wherein R represents a C-C covalent bond or a divalent hydrocarbon group, preferably an alkylene, a cycloalkylene or an arylene, e.g., phenylene, and $R^1$, $R^2$, $R^3$ and $R^4$ independently represent hydrogen, an alkyl or an aryl. In the case where R is a C-C covalent bond, the bis(2-oxazoline) compound may be 2,2'-bis(2-oxazoline), 2,2'-bis(4-methyl-2-oxazoline) or 2,2'-bis(5-methyl-2-oxazoline). Examples of the bis(2-oxazoline) compound wherein R is a hydrocarbon group are 1,2-bis(2-oxazolinyl-2)ethane, 1,4-bis(2-oxazolinyl-2)butane, 1,6-bis(2-oxazolinyl-2)hexane, 1,8-bis(2-oxazolinyl-2)octane, 1,4-bis(2-oxazolinyl-2)-cyclohexane, 1,2-bis(2-oxazolinyl-2)benzene, 1,3-bis(2-oxazolinyl-2)benzene, 1,4-bis(2-oxazolinyl-2)benzene, 1,2-bis(5-methyl-2-oxazolinyl-2)benzene, 1,3-bis(5-methyl-2-oxazolinyl-2)benzene, 1,4-bis(5-methyl-2-oxazolinyl-2)-benzene and 1,4-bis(4,4'-dimethyl-2-oxazolinyl-2)benzene. These may be used as a mixture of two or more.

According to the invention, the bis(2-oxazoline) compound is reacted with an organic reactive compound which has at least one active hydrogen in the molecule. The reactive compound specifically includes a sulfonamide, an acid imide, an aromatic hydroxy-carboxylic acid and a bisphenol sulfone compound.

The sulfonamide usable in the invention includes an aliphatic sulfonamide such as methanesulfonamide or ethanesulfonamide, and an aromatic sulfonamide such as benzenesulfonamide, o-toluenesulfonamide, p-toluenesulfonamide, naphthalene-α-sulfonamide or naphthalene-β-sulfonamide. The sulfonamide further includes a cyclic sulfonamide, e.g., saccharin, which is readily obtainable by the oxidative cyclization of o-toluenesulfonamide.

The acid imide usable in the invention includes an open chain acid imide such as diacetamide and a cyclic acid amide such as succinimide, glutarimide, parabanic acid, hydantoin, dimethylhydantoin, isocyanuric acid, phthalimide or maleinimide. The cyclic imide is preferred among these acid imides.

The aromatic hydroxy-carboxylic acid used in the invention includes benzene derivatives, for example, salicylic acid, m-hydroxybenzoic acid, p-hydroxybenzoic acid, o-cresotic acid, gallic acid, mandelic acid and tropic acid, and naphthalene derivatives, for example, α-hydroxynaphthoic acid and β-hydroxynaphthoic acid.

The bisphenol sulfone compound usable in the invention includes 4,4'-dihydroxydiphenylsulfone (bisphenol S) and 3,3'-dihydroxydiphenylsulfone. The bisphenol sulfone compound may carry one or more substituents such as alkyls or halogens on either of the aromatic nuclei, as in tetrabromobisphenol S.

These reactive compounds may be used as a mixture of two or more.

According to the invention, the reactive compound may be in part replaced by a dicarboxylic acid. The use of such a dicarboxylic acid as a component of the reactive compound improves in particular the mechanical strength, especially the flexural, tensile and impact strength of the resultant cross-linked resin.

The dicarboxylic acid usable in the invention has the general formula:

HOOC-R'-COOH wherein R' is a divalent hydrocarbon group and is fusible at the reaction temperature, and includes aliphatic dicarboxylic acids such as malonic acid, succinic acid, glutaric acid, adipic acid, pimelic acid, suberic acid, azelaic acid, sebacic acid, dodecandioic acid, dimer acid, eicosandioic acid or thiodipropionic acid, and aromatic dicarboxylic acids such as phthalic acid, isophthalic acid, terephthalic acid, naphthalenedicarboxylic acid, diphenylsulfonedicarboxylic acid or diphenylmethanedicarboxylic acid. These may also be used as a mixture of two or more. It is preferable that from about 5 mole % to 95 mole % of the reactive compound is replaced by the dicarboxylic acid.

According to the invention, the bis(2-oxazoline) compound and the reactive compound, either or both of them being hereinafter often referred to as reactants, are reacted at an elevated temperature in a molar ratio of the reactive compound to the bis(2-oxazoline) compound of not more than about 2, preferably in the range of about 1 to about 0.2, to provide the cross-linked resin.

Furthermore, according to the invention, the cross-linking or curing reaction is preferably carried out in the presence of a catalyst to shorten the curing or gellation time and/or to lowers the reaction temperature.

Various inorganic and organic compounds are effective as the catalyst, and the first group of catalysts specifically includes a phosphorous acid ester, an organic phosphonous acid ester and an inorganic salt. Among these a phosphorous acid ester is most preferred particularly because of its high catalytic activity and high solubility in the reaction mixture.

The phosphorous acid ester is preferably a diester and triester such as triphenyl phosphite, tris(nonylphenyl)phosphite, triethyl phosphite, tri-n-butyl phosphite, tris(2-ethylhexyl)phosphite, tristearyl phosphite, diphenylmonodecyl phosphite, tetraphenyl dipropyleneglycol diphosphite, tetraphenyltetra(tridecyl)pentaerythritol tetraphosphite, diphenyl phosphite, 4,4'-butylidenebis(3-methyl-6-t-butylphenyl-di-tridecyl)phosphite and bisphenol A pentaerythritol phosphite. These may be used as a mixture of two or more. Among these phosphites, those which have phenoxy or substituted phenoxy groups are particularly preferred.

Examples of organic phosphonous acid ester includes esters of an aliphatic or aromatic phosphonous acid, such as diphenyl phenylphosphonite, di(β-chloroethyl)β-chloroethylphosphonite or tetrakis(2,4-di-t-butylphenyl)-4,4'-diphenylendiphosphonite.

Various inorganic salts soluble in the reaction mixture are also effective as the catalyst. It is preferred that the salt has not water of crystallization. Preferred inorganic salts usable as the catalyst are composed of a monovalent or tetravalent cation (inclusive of polyatomic cations, e.g., vanadyl or zirconyl) such as lithium, potassium, sodium, magnesium, calcium, titanium, zirconium, vanadium, chromium, manganese, iron, cobalt, nickel, copper, zinc, cadmium, aluminum, tin or cerium, with an anion such as a halide, a nitrate, a sulfate or a chlorate. Among these salts, cupric chloride, vanadium chloride, vanadyl chloride, cobalt nitrate, zinc chloride, manganese chloride and bismuth chloride exhibit excellent catalytic activity.

The second group of catalysts used in the invention includes an oxazoline ring-opening polymerization catalyst such as a strong acid, a sulfonic acid ester, a sulfuric acid ester or an organic halide which contains at least one halomethyl group in the molecule. The oxazoline ring-opening polymerization catalyst is already known, as described in, for example, Polymer J., Vol. 3, No. 1, pp. 35–39 (1972) and Polymerization Reaction Treatize Course 7, Ring-Opening Polymerization II, pp. 165–189, Kagaku Dojin (1973).

More specifically, the strong acid includes an oxoacid such as phosphorous acid, sulfuric acid or nitric acid, a hydroacid such as hydrochloric acid or hydrogen sulfide, and an organic strong acid such as phenyl phosphorous acid, methanesulfonic acid, benzenesulfonic acid, p-toluenesulfonic acid, dodecylbenzenesulfonic acid, naphthalene-α-sulfonic acid, naphthalene-β-sulfonic acid, sulfanilic acid or phenylphosphonic acid.

The sulfonic acid ester includes methyl p-toluenesulfonate and ethyl p-toluenesulfonate. The sulfuric acid ester includes dimethylsulfuric acid and diethylsulfuric acid.

Preferred examples of the organic halide as defined above are a monohaloalkane and a polyhaloalkane such as methyl iodide, butyl chloride, butyl bromide, butyl iodide, lauryl bromide, allyl bromide or ethane tetrabromide. Other examples of the organic halide are monoor polyhalomethylbenzenes, e.g., benzyl bromide and p,p'-dichloromethylbenzene. The organic halide as the catalyst further includes a haloalkane which has a hydroxyl and/or a carboxyl group in the molecule, such as α-bromopropionic acid, 2,3-dibromopropanol or α-bromobutyric acid.

Among the above catalysts, the phosphorous acid ester and sulfonic acid ester are preferred.

The catalyst is used in amounts of 0.1–5% by weight, preferably 0.3–3% by weight based on the weight of a mixture of the bis(2-oxazoline) compound and the reactive compound.

In the reaction of the invention, the bis(2-oxazoline) compound and the reactive compound may be first mixed and then heated to melt together, or each of them may be first heated to melt and then mixed together, and when necessary, followed by further heating. The catalyst may also be added at any stage. For instance, the catalyst may be added to either the bis(2-oxazolin) compound or the reactive compound, or the catalyst may be added to a mixture of the reactants before, during or after heating to melt.

The reaction temperature at which the cross-linking reaction proceeds depends on the individual reactants, i.e., the bis(2-oxazoline) compound and the reactive compound as well as the catalyst used, and hence it is not specifically limited, however, usually it is not lower than about 100° C., preferably in the range of about 130° C. to 230° C. The reaction time or gellation time also varies depending on the individual reactants as well as the catalyst used, but usually in the range of about 10 seconds to 3 hours.

According to the invention, cross-linked resins including reinforcements and/or fillers are also obtainable, for example, by mixing the reinforcement and/or filler with a mixture of the bis(2-oxazoline) compound, the reactive compound and the catalyst, and then by heating the resultant mixture to cause the cross-linking reaction.

As the reinforcement, fibrous one which is in use in the ordinary plastic industry is usable. Specific examples of such reinforcement are inorganic fibers such as glass fibers, carbon fibers, quartz fibers, ceramic fibers, zirconia fibers, boron fibers, tungsten fibers, molybdenum fibers, steel fibers, berylium fibers and asbestos fibers, natural fibers as cotton, flax, hemp, jute or sisal hemp, and synthetic fibers having heat-resistance at the reaction temperature such as polyamide fibers or polyester fibers. In order to improve adhesion to the cross-linked resin, the fibrous reinforcement may be treated in advance with, for example, chromium compounds, silane, vinyltriethoxysilane or aminosilane.

The amount of the reinforcement may be selected, for example, upon the viscosity of the molten mixture, the reinforcement used, the requirements for cured products, etc., however, it is usually in the range of about 3–95% by weight, prferably about 5–80% by weight based on the mixture of the bis(21 -oxazoline) compound and the reactive compound.

Various fillers may also be incorporated into the cross-linked resin. Preferred examples of the filler include oxides such as silica, alumina or titanium dioxide, hydroxides such as aluminum hydroxide, carbonates such as calcium carbonate or magnesium carbonate, silicates such as talc, clay, glass beads or bentonite, carbon materials such as carbon black, metal powders such as iron powder or aluminum powder. The amount of the filler may be selected as in the case of the reinforcement, and it is usually in the range of about 3–500% by weight, preferably about 5–200% by weight based on the mixture of the reactants.

The cross-linked resin produced according to the present invention has excellent physical properties inclusive of mechanical strength, abrasion strength, heat-resistance and electrical properties as well as excellent chemical properties, especially an excellent heat-resistance and a very small water absorptivity. Furthermorte, according to the invention, cross-linked resin provided with a wide range of physical and chemical properties are obtainable by selecting the bis(2-oxazoline) compound and the reactive compound and the molar ratio therebetween. For example, the partial replacement of the reactive compound by the dicarboxylic acid provides the cross-linked resin having a particularly improved heat-resistance and mechanical properties.

Furthermore, the present process permits a rapid curing of the two reactants, so that the reaction system is suitably applicable to the reactive injection molding (RIM).

Therefore, The cross-linked resin may be usable for the production of machinery parts such as rolls and gears and embedded moldings of electrical machinery and apparatus parts as well as for electric insulating materials and dental uses. The cross-linked resin of the invention may further find applications in, for example, adhesives and various coating compositions.

Furthermore, the cross-linked resin which includes therein reinforcements and/or fillers provides resin molds with superior mechanical properties, especially outstanding toughness, and heat-resistance to conventional thermosetting resins. Therefore, cured products according to the invention finds applications not only in the application fields for conventional fiber-reinforced or filler-containing plastics, such as applications of aircraft, craft, railway vehicles, automobiles, civil engineering, construction and building, electrical and electronic appliances, anti-corrosion equipment, sporting and leisure goods, medical and industrial parts, but also in the new applications where conventional fiber-reinforced and filler-containing plastics have failed to achieve application development.

The present invention will be more easily understood with reference to the following examples, which however are intended to illustrate the invention only and are not to be construed as limiting the scope of the invention. In the examples, the thermal deflection temperature was measured over a load of 18.6 kg applied to a sample resin sheet, and the water absorption was measured by the increase in weight of a sample in the form of disc after immersing in water at 23° C. for 24 hours.

EXAMPLE 1

A mixture of 36 g (0.17 mole) of 1,3-bis(2-oxazolinyl-2)benzene, 14 g (0.11 mole) of dimethylhydantoin and 1 g of triphenyl phosphite were placed in a test tube and heated with occasional stirring in an oil bath of 200° C. After 10 minutes, the temperature of the mixture reached 190° C. and after 18 minutes the mixture gelled at 217° C. accompanying the generation of reaction heat.

The cured resin was transparent, hard and pale ambercolored.

EXAMPLE 2

A mixture of 15.2 g (0.07 mole) of 1,3-bis(2-oxazolinyl-2)benzene, 4.8 g (0.035 mole) of p-hydroxybenzoic acid and 0.2 g of a catalyst shown below were weighed into a test tube and heated with stirring in an oil bath of 150° C.

The gelation times by the second required for the molten mixture to gel after the mixture has reached 120° C. were as follows:
p-Toluenesulfonic acid 160
Methyl p-toluenesulfonate 120
Dimethylsulfuric acid 95
α-Bromopropionic acid 220

EXAMPLE 3

A mixture of 15.3 g (0.07 mole) of 1,3-bis(2-oxazolinyl-2)benzene, 4.7 g (0.05 mole) of succinimide and 0.2 g of a catalyst shown below were weighed into a test tube and heated with stirring in an oil bath of 150° C.

The gelation times by the second required to gel after the mixture has reached 120° C. were as follows:
p-Toluenesulfonic acid 280
Methyl p-toluenesulfonate 175
Dimethylsulfuric acid 105

EXAMPLE 4

A mixture of 37.5 g (0.17 mole) of 1,3-bis(2-oxazolinyl-2)benzene and 12.5 g (0.05 mole) of 4,4'-dihydroxydiphenylsulfone were placed in a beaker and was heated in an oil bath of 180° C. to melt the mixture. When the molten mixture reached 150° C., 0.5 g of a catalyst shown below was added to the mixture, and the gelation time by the second was measured. The results are shown below.
p-Toluenesulfonic acid 35
Dimethylsulfuric acid 25
α-Bromopropionic acid 105

EXAMPLE 5

A 10 g powdery mixture of 1,3-bis(2-oxazolinyl-2)benzene and an aromatic hydroxy-carboxylic acid as shown below with a molar ratio of the carboxylic acid to the bis(2-oxazoline) compound of 1:2, and 0.2 g of triphenyl phosphite were weighed into a test tube, and then were placed in an oil bath of 180° C.

The gelation times by the second required to gel after the mixture has reached 150° C. were as follows:
 Salicylic acid 330
 p-Hydroxybenzoic acid 1020
 β-Hydroxynaphthoic acid 300

The cured resins were transparent, hard and pale ambercolored.

EXAMPLE 6

A mixture of 130 g (0.60 mole) of 1,3-bis(2-oxazolinyl-2)benzene, 44 g (0.30 mole) of phthalimide and 3.5 g of triphenyl phosphite was heated to 185° C. to melt. Then the mixture was poured into a mold which had a cavity of 0.3 cm×30 cm×13 cm and had been in advance heated to 215° C., and then was left standing in an oven at 215° C. for 1 hour to allow the mixture to form a cross-linked resin.

After cooling, the cured sheet 3 mm in thickness was taken out of the mold, and was subjected to measurements of the properties, which are shown below.
 Thermal deflection temperature 183° C.
 Water absorption 0.3%
 Volume resistivity $3.4 \times 10^{16}$ Ωcm
 Dielectric constant ($10^6$ Hz) 3.36
 Dielectric loss tangent ($10^6$ Hz) 0.94
 Dielectric breakdown strength 16 KV/mm

EXAMPLE 7

A mixture of 65 g (0.30 mole) of 1,3-bis(2-oxazolinyl-2)benzene, 65 g (0.30 mole) of 1,4-bis(2-oxazolinyl-2)benzene, 29 g (0.20 mole) of phthalimide and 2.4 g of triphenyl phosphite was heated to 180° C. to melt. Then the mixture was poured into the same mold as used in Example 6 in advance heated to 215° C., and then was cured at 215° C. for 1 hour.

After cooling, the cured sheet 3 mm in thickness was found to have the following properties:
 Thermal deflection temperature 179° C.
 Water absorption 0.34%

EXAMPLE 8

A mixture of 130 g (0.60 mole) of 1,3-bis(2-oxazolinyl-2)benzene, 15 g (0.10 mole) of phthalimide, 17 g (0.10 mole) of isophthalic acid and 1.6 g of triphenyl phosphite was heated to 160° C. to melt. Then the mixture was poured into the same mold as used in Example 6 in advance heated to 200° C., and then was cured at 200° C. for 30 minutes.

After cooling, the cured sheet 3 mm in thickness was found to have the following properties:
 Thermal deflection temperature 164° C.
 Water absorption 0.3%
 Flexural strength 10 kgf/mm$^2$
 Flexural modulas 570 kgf/mm$^2$

EXAMPLE 9

A mixture of 130 g (0.60 mole) of 1,3-bis(2-oxazolinyl-2)benzene, 55 g (0.40 mole) of p-hydroxybenzoic acid and 2.5 g of triphenyl phosphite was heated to 130° C. to melt. Then the mixture was poured into the same mold as used in Example 6 in advance heated to 200° C., and then was left standing in an oven at 200° C. for 1 hour to allow the mixture to form a cured sheet.

After cooling, the cured sheet 3 mm in thickness was taken out of the mold, and was subjected to measurements of the properties, which are shown below.
 Thermal deflection temperature 163° C.
 Water absorption 0.4%
 Flexural strength 12.2 kgf/mm$^2$
 Flexural modulas 450 kgf/mm$^2$

EXAMPLE 10

A mixture of 135 g (0.625 mole) of 1,3-bis(2-oxazolinyl-2)benzene, 35 g (0.25 mole) of p-hydroxybenzoic acid and 5.1 g of triphenyl phosphite was heated to 150° C. to melt. Then the mixture was poured into the same mold as used in Example 6 in advance heated to 200° C., and then was left standing in an oven at 200° C. for 2 hour to allow the mixture to form a cross-linked resin.

After cooling, the cured sheet 3 mm in thickness was taken out of the mold, and was subjected to measurements of the properties, which are shown below.
 Thermal deflection temperature 226° C.
 Water absorption 0.10%
 Flexural strength 8 kgf/mm$^2$
 Flexural modulas 530 kgf/mm$^2$

EXAMPLE 11

A mixture of 54 g (0.25 mole) of 1,3-bis(2-oxazolinyl-2)benzene, 54 g (0.25 mole) of 1,4-bis(2-oxazolinyl-2)benzene, 47 g (0.25 mole) of β-hydroxynaphthoic acid and 3.0 g of triphenyl phosphite was heated to 160° C. to melt. Then the mixture was poured into the same mold as used in Example 6 in advance heated to 210° C., and then was left standing in an oven at 210° C. for 30 minutes to allow the mixture to form a cured sheet.

After cooling, the cured sheet 3 mm in thickness was taken out of the mold, and was subjected to measurements of the properties, which are shown below.
 Thermal deflection temperature 187° C.
 Water absorption 0.22%
 Flexural strength 12.5 kgf/mm$^2$
 Flexural modulas 590 kgf/mm$^2$
 Volume resistivity $1.0 \times 10^{16}$ Ωcm
 Dielectric constant ($10^6$ Hz) 3.5
 Dielectric loss tangent ($10^6$ Hz) $0.9 \times 10^{-2}$
 Dielectric breakdown strength 16 KV/mm

EXAMPLE 12

A mixture of 130 g (0.60 mole) of 1,3-bis(2-oxazolinyl-2)benzene, 41 g (0.30 mole) of salicylic acid and 1.5 g of triphenyl phosphite was heated to 140° C. to melt. Then the mixture was poured into the same mold as used in Example 6 in advance heated to 200° C., and then was left standing in an oven at 200° C. for 1 hour to allow the mixture to form a cross-linked resin.

After cooling, the cured sheet 3 mm in thickness was found to have the following properties:
 Thermal deflection temperature 175° C.
 Water absorption 0.26%

EXAMPLE 13

A mixture of 135 g (0.625 mole) of 1,3-bis(2-oxazolinyl-2)benzene and 35 g (0.25 mole) of salicylic acid was heated to melt, and 1.7 g of p-toluenesulfonic acid was added thereto with an effective stirring to provide a uniform mixture. The mixture was then poured into the same mold as used in Example 6 in advance heated to 200° C., and then was left standing in an oven at 200° C. for 2 hours to allow the mixture to form a cross-linked resin.

After cooling, the cured sheet 3 mm in thickness was found to have the following properties:
Thermal deflection temperature 208° C.
Water absorption 0.22%
Flexural strength 11 kgf/mm$^2$
Flexural modulas 590 kgf/mm$^2$

EXAMPLE 14

A mixture of 130 g (0.60 mole) of 1,3-bis(2-oxazolinyl-2)benzene, 28 g (0.20 mole) of p-hydroxybenzoic acid, 29 g (0.20 mole) of adipic acid and 3.7 g of triphenyl phosphite was heated to 130° C. to melt. Then the mixture was poured into the same mold as used in Example 6 in advance heated to 200° C., and then was cured at 200° C. for 30 minutes.

After cooling, the cured sheet 3 mm in thickness was found to have the following properties:
Thermal deflection temperature 122° C.
Water absorption 0.53%
Flexural strength 21 kgf/mm$^2$
Flexural modulas 480 kgf/mm$^2$

EXAMPLE 15

A mixture of 135 g (0.625 mole) of 1,3-bis(2-oxazolinyl-2)benzene, 26 g (0.19 mole) of p-hydroxybenzoic acid, 13 g (0.06 mole) of sebacic acid and 2.6 g of triphenyl phosphite was heated to 140° C. to melt. Then the mixture was poured into the same mold as used in Example 6 in advance heated to 200° C., and then was cured at 200° C. for 2 hours.

The cured sheet was found to have the following properties:
Thermal deflection temperature 206° C.
Water absorption 0.4%
Flexural strength 21 kgf/mm$^2$
Flexural modulas 550 kgf/mm$^2$

EXAMPLE 16

A mixture of 113 g (0.53 mole) of 1,3-bis(2-oxazolinyl-2)benzene and 38 g (0.15 mole) of 4,4'-dihydroxydiphenyl sulfone was heated to 130° C., and then 0.75 g of methyl p-toluenesulfonate was added thereto with an efective stirring. Then the resulting mixture was poured into the same mold as used in Example 6 in advance heated to 180° C., and then was cured at 180° C. for 2 hours.

The cured sheet was found to have the following properties:
Thermal deflection temperature 270° C.
Water absorption 0.3%
Flexural strength 12 kgf/mm$^2$
Flexural modulas 550 kgf/mm$^2$

EXAMPLE 17

A mixture of 97 g (0.45 mole) of 1,3-bis(2-oxazolinyl-2)benzene, 38 g (0.15 mole) of 4,4'-dihydroxydiphenyl sulfone, 22 g (0.15 mole) of adipic acid and 1.6 g of triphenyl phosphite was heated to 130° C. to melt. Then the mixture was poured into the same mold as used in Example 6 in advance heated to 200° C., and then was left standing in an oven at 200° C. for 1 hour to allow the mixture to form a cross-linked resin.

After cooling, the cured sheet was found to have the following properties:
Thermal deflection temperature 138° C.
Water absorption 0.4%
Flexural strength 12.3 kgf/mm$^2$
Flexural modulas 440 kgf/mm$^2$

EXAMPLE 18

A mixture of 105 g (0.49 mole) of 1,3-bis(2-oxazolinyl-2)benzene and 45 g (0.25 mole) of saccharin was heated to 155° C., and then 2.2 g of triphenyl phosphite was added thereto with an effective stirring. Then the resulting mixture was poured into the same mold as used in Example 6 in advance heated to 210° C., and then was cured at 210° C. for 1 hour.

The cured sheet was found to have the following properties:
Thermal deflection temperature 188° C.
Water absorption 0.1%
Flexural strength 9 kgf/mm$^2$
Flexural modulas 680 kgf/mm$^2$

EXAMPLE 19

A mixture of 34.6 g (0.16 mole) of 1,3-bis(2-oxazolinyl-2)benzene and 27.4 g (0.16 mole) of p-toluenesulfonamide and 0.43 g of triphenyl phosphite was heated to 170° C. and then the resulting mixture was placed in a cylindrical mold provided with a heater. When the mixture reached a temperature of 110° C., it became transparent and gelled after 23 minutes. After heating for further 20 minutes, the mixture was left standing for cooling. The thus obtained product was taken out of the mold, which was found to have a Shore hardness D of 94.

EXAMPLE 20

A mixture of 147 g (0.68 mole) of 1,3-bis(2-oxazolinyl-2)benzene, 50 g (0.34 mole) of adipic acid, 11.6 g (0.068 mole) of p-toluenesulfonamide and 2.1 g of triphenyl phosphite was placed in a stainless steel beaker and was heated to melt in an oil bath.

When the mixture reached a temperature of 115° C., the mixture was poured into the same mold as used in Example 6 in advance heated to 200° C., and then was left standing in an oven at 200° C. for 40 minutes to allow the mixture to form a cross-linked resin.

After cooling, the cured sheet was found to have a thermal deflection temperature of 98° C.

EXAMPLE 21

A 71 g quantity (0.66 mole) of 1,3-bis(2-oxazolinyl-2)benzene, 9 g (0.13 mole) of p-hydroxybenzoic acid, 9 g (0.13 mole) of salicylic acid, 11 g (0.11 mole) of sebacic acid and 2 g of triphenyl phosphite were mixed thoroughly in a mortar, and the mixture was heated to about 130° C. to be molten. On a hot plate heated at 120°–130° C. were placed a polyester mold-releasing film and then glass plain-woven cloth MG 253A (Asahi Fiber Glass K.K.) in 14 layers.

The resin was poured on the layers of glass cloth to impregnate them with the resin uniformly while degassing with the use of an aluminum degassing roller for lamination. Thereafter the layers of glass cloth were covered with a polyester mold-releasing film, followed by allowing to cool to room temperature. The resultant resin-impregnated layers of glass cloth were substantially tack-free.

After removing the polyester mold-releasing films, the layers of glass cloth were placed between plate molds having on thier surfaces coatings of ordinary silicone-based releasing agent, and cured at about a temperature of 200° C. under a pressure of 20 kg/cm$^2$ for 1 hour to provide a flat sheet about 3 mm in thickness.

A test specimen was cut out of the flat sheet and was subjected to measurement of physical properties. The tensile strength, flexural strength and flexural modulus were measured in accordance with JIS K 6911, and the tensile modulus and tensile elongation in accordance with JIS K 7113, while the compression strength and Izod impact strength in accordance with JIS K 7208 and JIS K 7110, respectively. The content of resin was determined in accordance with JIS K 6919. The results are as follows:

Resin content 42.8% by weight
Tensile strength 32.7 kgf/mm$^2$
Tensile modulus 2180 kgf/mm$^2$
Tensile elongation 1.93%
Flexural strength 48.1 kgf/mm$^2$
Flexural modulas 2170 kgf/mm$^2$
Compression strength 56.0 kgf/mm$^2$
Izod impact strength 77 kg.cm/cm$^2$

EXAMPLE 22

A flat sheet was formed in the same manner as in Example 21 except the use of carbon fiber plain-woven cloth #3101 (Toho Rayon K.K.) in 12 layers in place of the glass fiber plain-woven cloth. The flat sheet was subjected to measurement of physical properties in the same manner as in Example 21 except the resin content which was determined by immersing the sheet in sulfuric acid to decompose and remove the resin therefrom and by weighing the resulting residue. The results are as follows:

Resin content 41.6% by weight
Tensile strength 62.8 kgf/mm$^2$
Tensile modulus 5840 kgf/mm$^2$
Tensile elongation 1.09%
Flexural strength 96.0 kgf/mm$^2$
Flexural modulas 5030 kgf/mm$^2$
Compression strength 52.1 kgf/mm$^2$
Izod impact strength 65 kg.cm/cm$^2$

What is claimed is:

1. A process for producing a cross-linked resin which comprises: reacting a bis(2-oxazoline) compound with a reactive compound which has at least one active hydrogen in the molecule, the reactive compound being at least one aromatic hydroxy-carboxylic acid, in a molar ratio of the reactive compound to the bis(2-oxazoline) compound of not more than about 2, at an elevated temperature.

2. A process for producing a cross-linked resin as claimed in claim 1, wherein about 5 to about 95 mole % of the reactive compound is replaced by a dicarboxylic acid.

3. A process for producing a cross-linked resin as claimed in claim 1, wherein the reaction is carried out in the presence of a catalyst selected from the group consisting of a phosphorous acid ester, an organic phosphonous acid ester and an inorganic salt.

4. A process for producing a cross-linked resin as claimed in claim 1, wherein the reaction is carried out in the presence of an oxazoline ring-opening polymerization catalyst.

5. A process for producing a cross-linked resin as claimed in claim 4, wherein the oxazoline ring-opening polymerization catalyst is a strong acid, a sulfonic acid ester, a sulfuric acid ester or an organic halide which has at least one halomethyl group in the molecule.

6. A process for producing a cross-linked resin as claimed in claim 5, wherein the strong acid is an oxoacid, a hydroacid or an strong organic acid.

7. A process for producing a cross-linked resin as claimed in claim 5, wherein the sulfonic acid ester is an alkyl p-toluenesulfonate.

8. A process for producing a cross-linked resin as claimed in claim 5, wherein the sulfuric acid ester is a dialkylsulfuric acid.

9. A process for producing a cross-linked resin as claimed in claim 5, wherein the organic halide is a monohaloalkane.

10. A process for producing a cross-linked resin as claimed in claim 5, wherein the organic halide is α-haloalkanoic acid.

11. A process for producing a cross-linked resin as claimed in claim 6, wherein the strong organic acid is an alkanesulfonic acid or an arenesulfonic acid.

12. A process for producing a cross-linked resin as claimed in claim 1, wherein the catalyst is used in amounts of 0.1–5% by weight based on the weight of a mixture of the bis(2-oxazoline) compound and the reactive compound.

13. A process for producing a cross-linked resin as claimed in claim 1, wherein the bis(2-oxazoline) compound is reacted with the reactive compound in the presence of about 3–95% by weight of reinforcements based on the mixture of the bis(2-oxazoline) compound and the reactive compound.

14. A process for producing a cross-linked resin as claimed in claim 1, wherein the bis(2-oxazoline) compound is reacted with the reactive compound in the presence of about 3–500% by weight of fillers based on the mixture of the bis(2-oxazoline) compound and the reactive compound.

15. A process for producing a cross-linked resin as claimed in claim 1, wherein the molar ratio of the reactive compound to the bis(2-oxazoline) compound is in the range of about 1 to about 0.2.

16. The process for producing a cross-linked resin which comprises: reacting a bis(2-oxazoline) compound with an aromatic hydroxy-carboxylic acid in a molar ratio of the aromatic hydroxy-carboxylic acid to the bis(2-oxazoline) compound of not more than about 2, in the presence of a catalyst selected from the group consisting of a phosphorous acid ester, an organic phosphorous acid ester and an inorganic salt, at an elevated temperature.

17. The process for producing a cross-linked resin as claimed in claim 16, wherein the aromatic hydroxy-carboxylic acid is p-hydroxy benzoic acid.

18. The process for producing a cross-linked resin as claimed in claim 16, wherein the aromatic hydroxy-carboxylic acid is salicylic acid.

19. The process for producing a cross-linked resin as claimed in claim 16, wherein the aromatic hydroxy-carboxylic acid is β-hydroxynaphthoic acid.

20. The process for producing a cross-linked resin as claimed in claim 16, wherein the catalyst is a phosphorous acid ester.

21. The process for producing a cross-linked resin as claimed in claim 16, wherein the phosphorous acid ester is a phosphorous acid triester.

22. The process for producing a cross-linked resin as claimed in claim 21, wherein the phosphorous acid triester is triphenyl phosphite.

23. The process for producing a cross-linked resin as claimed in claim 16, wherein about 5 to about 95 mole % of the aromatic hydroxy-carboxylic acid is replaced by a dicarboxylic acid.

* * * * *